United States Patent [19]

Cain et al.

[11] Patent Number: 5,116,846
[45] Date of Patent: May 26, 1992

[54] N-ARALKYL PIPERIDINE DERIVATIVES AS PSYCHOTROPIC DRUGS

[75] Inventors: Gary A. Cain, New Castle; Paul J. Gilligan, Claymont; Sang W. Tam, Hockessin, all of Del.

[73] Assignee: Du Pont Merck Pharmaceutical Company, Wilmington, Del.

[21] Appl. No.: 500,573

[22] Filed: Mar. 28, 1990

[51] Int. Cl.$^5$ .......................................... A61K 31/445
[52] U.S. Cl. ................................... 514/317; 514/331
[58] Field of Search ............... 546/240, 230, 234, 236, 546/240; 514/317

[56] References Cited

U.S. PATENT DOCUMENTS 4,783,471 11/1988 Carr et al. ........................ 514/317
4,912,117 3/1990 Carr et al. ........................ 514/317

Primary Examiner—Mary C. Lee
Assistant Examiner—Joseph K. McKane

[57] ABSTRACT

There are provided N-aralkyl piperidine derivatives which are selective sigma receptor antagonists. These compounds and pharmaceutical compositions containing them are useful for treating physiological or drug induced psychosis or dyskinesia in a mammal.

6 Claims, No Drawings

N-ARALKYL PIPERIDINE DERIVATIVES AS PSYCHOTROPIC DRUGS

BACKGROUND OF THE INVENTION

1. Field of the Invention

This invention relates to disubstituted N-aralkyl piperidine derivatives useful as antipsychotic agents and pharmaceutical compositions containing them. Furthermore, this invention relates to methods of using these compounds in the treatment of physiological or drug induced psychosis or dyskinesia in a mammal.

2. Prior Art

U.S. Pat. No. 4,876,262 (Oinuma et al.) describes antiarrhythmic agents having the formula:

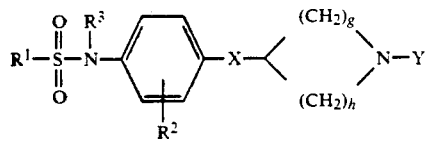

wherein:
- $R_1$ is lower alkyl or tolyl;
- $R_2$ is H, hydroxyl, lower alkoxy or lower alkyl;
- $R_3$ is H, lower alkyl, lower alkenyl, cycloalkyl or cycloalkylalkyl,
- X is —CO—, —CH$_2$— or —CHOH—;
- g and h independently are 1-3, with the proviso that g+h is 3 or 4; and
- Y is —A—B,
  [wherein A is: —(CH$_2$)$_n$ (n=1-5), straight chain $C_{1-5}$ alkylene and substituted with lower alkyl, phenyl or hydroxyl, straight chain C2-5 alkenylene, —(CH$_2$)$_k$—S— (k=2-5), or —(CH$_2$)$_p$CO (p=1-4), and wherein B is:

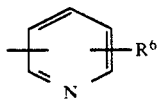

wherein $R^6$ is H, lower alkyl, lower alkoxy, cyano, imidazolyl, hydroxyl or halogen].

U.S. Pat. No. 4,254,127 (Vandenberk et al.) describe in pertinent part compounds of the formula:

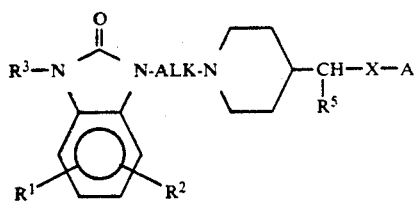

wherein:
- X is C=O, CHOH, CHO Acyl, CH$_2$, C(O alkyl)$_2$;
- ALK is lower alkylene radical; and
- Ar is aryl or heteroaryl.

These compounds are described as having potent serotonin-antagonistic and strong psychotropic activity and as being useful in the treatment of mental disorders and congestive diseases and as antiemetics.

U.S. Pat. No. 4,294,841 (Champseix et al.) describes antiarrhythmic, antidepressant and anxiolytic compounds of the formula:

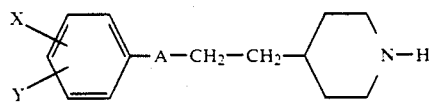

wherein:
- X and Y independently are H, halogen, C1-4 alkyl, C1-4 alkoxy, C1-4 alkylthio, CF$_3$, OH, NH$_2$, C1-4 monoalkylamino or amino groups substituted by one of the following:
  C1-4 alkyl sulfonyl, C1-5 alkyl carbonyl or aroyl; and
- A is CO, CHOH or CH$_2$.

EP 0,208,235 (Carr et al.) describes selective serotonin antagonist compounds of the formula:

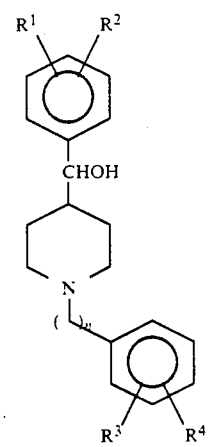

wherein:
- $R^1$-$R^4$ independently are H, C1-C6 alkyl, halogen, CF$_3$, OH, C1-C6 alkoxy or amino; and
- n is 2-4.

U.S. Pat. No. 4,283,404 (Carr et al.) describes antipsychotic agents which act due to dopamine antagonism, having the formula:

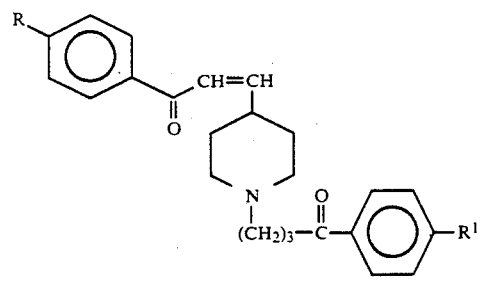

wherein:
- R is H, alkyl, alkoxy, halogen or CF$_3$; and
- $R^1$ is H or halogen.

Nagai et al., Chem. Pharm. Bull., 27 (5) 1159-1168 (1979) describe the synthesis of 1-substituted 2-[2-(p-fluorobenzoyl)ethyl]piperidine and related compounds. Related compounds include but are not limited to 1-ethyl-3-(p-fluorophenacyl) piperidine and 1-[3-(p-fluorobenzoyl)propyl]-3-(p-fluorophenacyl) pyrrolidine and 4-(p-fluorobenzoyl) piperidines which have CNS-depressing activities.

Unlike the prior art compounds, the compounds of the present invention are potent antipsychotic compounds which exert their effect through selective sigma receptor antagonism.

Traditionally, antipsychotic agents such as the phenothiazines and butyrophenones are potent dopamine receptor antagonists which are associated with a high incidence of side effects, particularly Parkinson-like motor movements or extra-pyramidal side effects (EPS) and dyskinesias including tardive dyskinesia at high doses. Many of these side effects are not reversible even after the dopamine receptor antagonist agent is discontinued.

The present invention relates to antipsychotic agents which act by selective antagonism of the sigma receptor rather than antagonism to the dopamine receptor. The present compounds therefore have a low potential for the typical movement disorders associated with known antipsychotic agents, while maintaining the ability to antagonize aggressive behavior and hallucinogenic-induced behavior and therefore are useful as antipsychotic and dyskinetic agents.

SUMMARY OF THE INVENTION

The sigma-selective antipsychotic/antidyskinetic compounds of the present invention are disubstituted N-aralkyl piperidine derivatives of the formula:

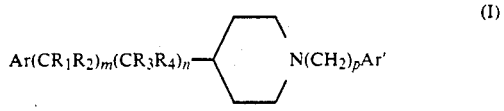

(I)

or a pharmaceutically acceptable salt thereof wherein:
$R_1$ and $R_3$ independently are H, alkyl of 1-3 carbon atoms, $NR_5R_6$, OH, alkoxy of 1-3 carbon atoms, $CO_2H$, carboalkoxy of 2-6 carbon atoms, halogen, CN, aryl, $CONR_7R_8$, $S(O)_qR_9$ (q=0-2) or $Ar''$;
$R_2$ and $R_4$ independently are H, alkyl of 1 to 3 carbon atoms;
$CR_1R_2$ or $CR_3R_4$ may be C=O provided that both cannot be C=O;
Ar, Ar' and Ar'' independently are phenyl optionally substituted with 1-5 substituents independently selected from the group consisting of:
  H, halogen, OH, alkoxy of 1-3 carbon atoms, $NR_{10}R_{11}$, SH, $S(O)_tR_{12}$ (t=0-2), haloalkyl of 1-3 carbon atoms and 1-7 halogen atoms, alkyl of 1-3 carbon atoms, $CO_2H$, carboalkoxy of 2-6 carbon atoms, $CO_2NR_{13}R_{14}$, CN, $NO_2$, $SO_2NH_2$ or $SO_3H$,
or Ar, Ar' and Ar'' independently are naphthyl, pyridyl, pyrimidyl, quinolinyl, isoquinolinyl, indolyl or indazolyl each optionally substituted by H, halogen or alkyl of 1 to 3 carbons;
$R_5$ to $R_{14}$ independently are H or alkyl of 1-3 carbon atoms;
m and n independently are 1-5; and
p is 1-2, provided that except as noted above, all other positions on the piperidine ring are substituted by H.

Preferred compounds are those compounds of Formula (I) wherein:
m plus n is 2 or 3; and/or
p is 1-2; and/or Ar and Ar' independently are phenyl optionally substituted with 1-3 substituents as listed above or naphthyl, pyridyl, pyrimidyl, quinolinyl or indolyl.
Specifically preferred compounds are:
(a)   1-Benzyl-4-(2'-(4''-fluorophenyl)-2'-hydroxyethyl) piperidine or the hydrochloride salt thereof;
(b)   1-Benzyl-4-(2'-(4''-fluorophenyl)-2'-oxoethyl) piperidine or the maleate salt thereof;
(c)   1-Benzyl-4-(2'-(4''-fluorophenyl)-1'-oxoethyl) piperidine, or the maleate salt thereof;
(d)   1-(4'-Pyridylmethyl)-4-(2'(4''-fluorophenyl)-1'-oxoethyl)piperidine, or the maleate salt thereof.

Further this invention relates to pharmaceutical compositions comprising a pharmaceutically acceptable carrier and an effective amount of a compound of Formula (I).

Also provided are methods of treating physiological or drug induced psychosis or dyskinesia in a mammal comprising administering to the mammal an effective amount of a compound of the formula:

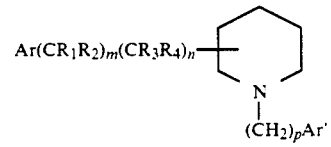

or a pharmaceutically acceptable salt thereof wherein:
$R_1$–$R_4$, m, n and p, Ar, Ar' and Ar'' are as defined above.

Further provided are processes for preparing the compounds of Formula (I) as set forth below.

DETAILED DESCRIPTION OF THE INVENTION

Select compounds of this invention, Formula (I) wherein $R_2$ is $NR_5R_6$, or $CR_1R_2$ is C=O or CHOH (m=1) may be prepared according to Scheme I. An alcohol of Formula (IV) may be oxidized with an oxidizing agent in an inert solvent to give an aldehyde of Formula (V). Oxidizing agents include but are not limited to $CrO_3$, $CrO_3$-$H_2SO_4$, $MnO_2$, $(COCl)_2$-DMSO-$Et_3N$, pyridinium chlorochromate, pyridinium dichromate, or $CrO_3$-pyridine. The choice of oxidizing agent follows the prior art summarized by J. March ("Advanced Organic Chemistry," 3rd ed., (New York:J. Wiley and Sons, 1985), pp 1048-1120). Inert solvents include haloalkanes of 1 to 6 carbons (preferably $CH_2Cl_2$) or ethereal solvents (such as diethyl ether or tetrahydrofuran). Reaction temperatures range from about 25° to 100° C. Aldehydes of Formula (V) may be prepared by reduction of a compound of Formula (III) where Z is cyano or carboalkoxy of 2 to 6 carbons. Suitable reducing agents include dialkylaluminum hydrides (preferably diisobutylaluminum hydride), trialkoxy lithium aluminum hydrides (preferably LiAlH(t-Bu)$_3$), dialkylboranes, LiAlH$_4$, B$_2$H$_6$, AlH$_3$ or NaBH$_4$-AlCl$_3$. The choice of reducing agent follows the prior art summarized in the above March reference. Inert solvents include, but are not limited to aromatic hydrocarbons of 6 to 10 carbons (preferably toluene) or ethereal solvents of 4 to 10 carbons (preferably tetrahydrofuran). Reaction temperatures range from about −80° to 200° C., preferably −80° to 50° C. Aldehydes of Formula (V) may be reacted with aryl metal compounds of the formula ArM (where Ar is defined above and M is an alkali metal (preferably Li), an alkaline earth metal halide (preferably MgCl or MgBr or ZnCl) or a transition metal halide (preferably CeCl) to give alcohols of Formula (VI). This last transformation requires an inert solvent such as an ethereal solvent of 4 to 10 carbons (preferably tetrahydrofuran), an aromatic hydrocarbon of 6 to 10 carbons or a hydrocarbon of 5 to 10 carbons. Reaction temperatures range from about −70° to 200° C., preferably 60° to 120° C. Alcohols of Formula (VI) may be oxidized to ketones of Formula (VII) using the reaction conditions described for the synthesis of aldehydes of Formula (V) above. Ketones of Formula (VII) may be converted to amines of Formula (VIII) by reaction with amines of Formula $HNR_5R_6$ in the presence of a reducing agent in an inert solvent. Such reducing agents include alkali metal borohydrides, alkali metal cyanoborohydrides (preferably $NaBH_3CN$), molecular hydrogen and a noble metal catalyst, diimide or its precursors, or any of the reducing agents described above for the preparation of aldehydes of Formula (V). Reaction solvents include hydroxyalkanes of 1 to 10 carbons, ethereal solvents of 4 to 10 carbons, hydrocarbons of 5 to 10 carbons, or aromatic hydrocarbons to 6 to 10 carbons. $R_5$ and $R_6$ may independently by H, alkyl of 1 to 6 carbons, or taken together, alkylene of 3 to 8 carbons. Reaction temperatures range from about −70° to 200° C., preferably 0° to 80° C. The choice of reaction conditions follows the prior art summarized in the above March reference (pp. 798–800).

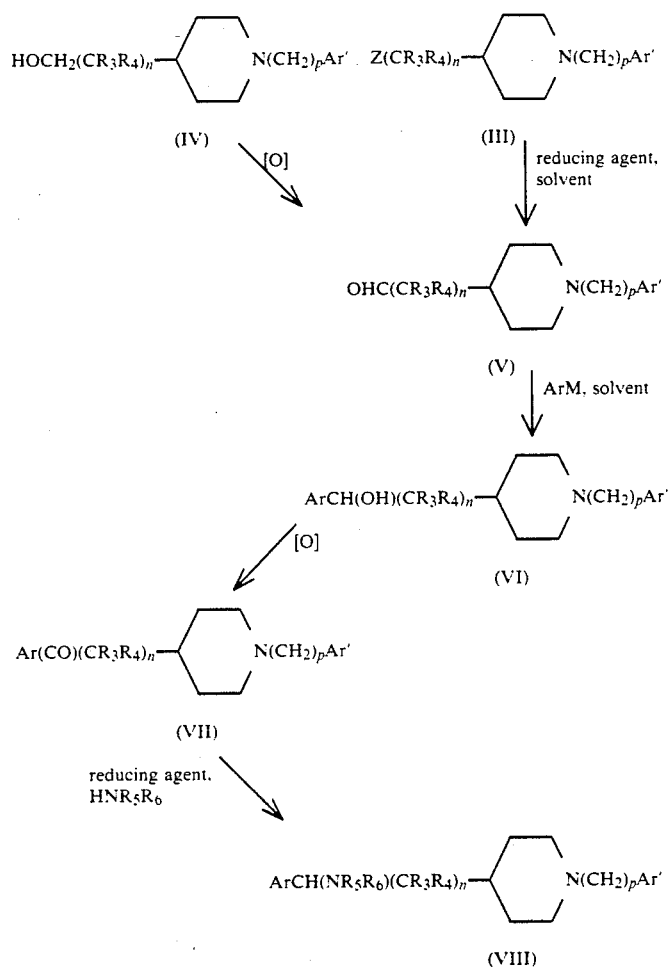

Select compounds of this invention, Formula (I), wherein $R_4$ is $NR_5R_6$, or $CR_3R_4$ is C=O or CHOH (n=1), may be prepared according to Scheme II. Alcohols of Formula (IX) may be oxidized to aldehydes of Formula (X) using the reaction conditions and reagents specified in the preparation of aldehydes of Formula (V). Aldehydes of Formula (X) may be converted to alcohols of Formula (XI) using an aralkyl metal compound of Formula $Ar(CR_1R_2)m^M$ where Ar, $R_2$, and $R_2$ are defined above and M is defined to be the same as in ArM used in the preparation for alcohols of Formula (VI). Similarly the reaction conditions used for the synthesis of alcohols (VI) apply to alcohols (XI). Alcohols (XI) may be oxidized to ketones of Formula (XII) using the reagents and conditions specified for the preparation of ketones (VII) above. Ketones of Formula (XII) may be converted to amines of Formula (XIII) using reagents and conditions specified for the preparation of amines (VIII) above.

Scheme II

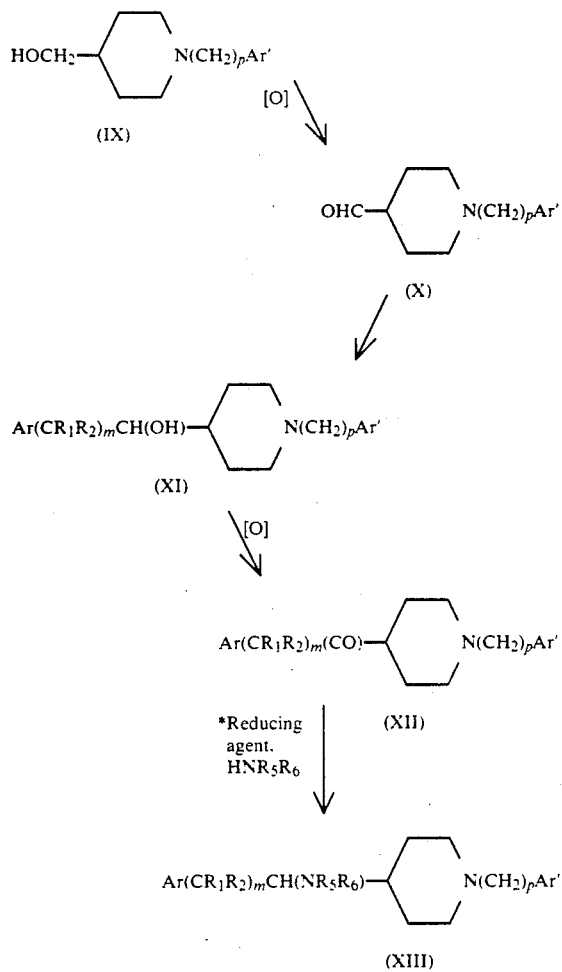

Some of the compounds of this invention may be prepared according to Scheme III. Compounds of Formula (XV) (where Y is an electron-withdrawing group such as nitro, carboxy, carboalkoxy, cyano, alkylthio, arylthio, alkylsulfonyl, arylsulfonyl) are treated with a base, then reacted with a compound of Formula (XIV) in an inert solvent to give compounds of Formula (XIX). The leaving group K in Formula (XIV) may be halogen, alkylsulfonyloxy, arylsulfonyloxy, trifluoromethylsulfonyloxy, or acyloxy groups.

Scheme III

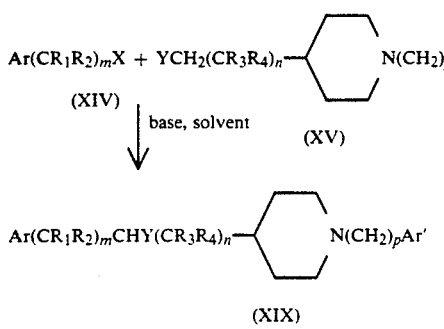

Scheme III
—continued

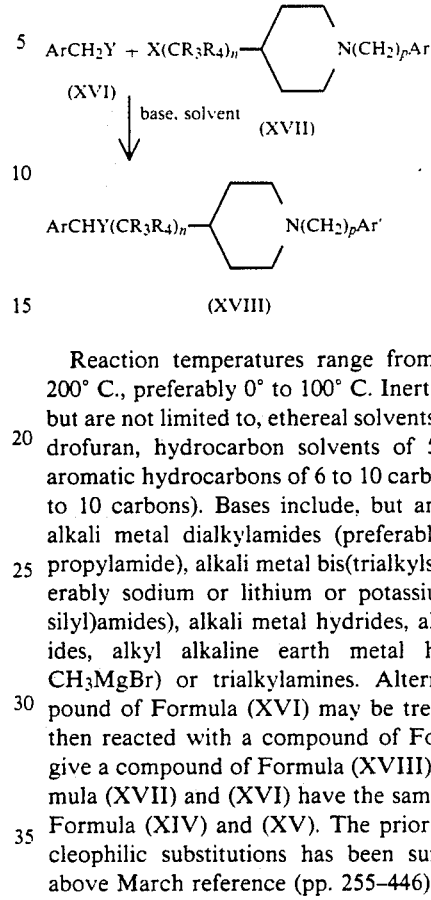

Reaction temperatures range from about −78° to 200° C., preferably 0° to 100° C. Inert solvents include, but are not limited to, ethereal solvents (such as tetrahydrofuran, hydrocarbon solvents of 5 to 10 carbons, aromatic hydrocarbons of 6 to 10 carbons, alcohols of 1 to 10 carbons). Bases include, but are not limited to, alkali metal dialkylamides (preferably lithium di-isopropylamide), alkali metal bis(trialkylsilylamides) (preferably sodium or lithium or potassium bis(trimethylsilyl)amides), alkali metal hydrides, alkali metal alkoxides, alkyl alkaline earth metal halides (such as $CH_3MgBr$) or trialkylamines. Alternatively, a compound of Formula (XVI) may be treated with a base, then reacted with a compound of Formula (XVII) to give a compound of Formula (XVIII). X and Y in Formula (XVII) and (XVI) have the same definitions as in Formula (XIV) and (XV). The prior art for these nucleophilic substitutions has been summarized in the above March reference (pp. 255–446).

Some compounds of this invention may be prepared according to Scheme IV. Pyridines of Formula (XX) may be converted to the corresponding pyridinium salts by reaction with a compound of Formula $Ar'(CH_2)_pX$ where X is a halogen, alkylsulfonyloxy, arylsulfonyloxy or acyloxy group. The salts may be formed with or without an inert solvent. When a solvent is used, it may be an alkanenitrile (such as acetonitrile), a halocarbon of 1 to 6 carbons (such as $CH_2Cl_2$ or $CHCl_3$), an alcohol of 1 to 10 carbons or an ethereal solvent of 4 to 10 carbons. Reaction temperatures range from about 0° to 200° C., preferably 50° to 100° C. Salts of Formula (XXI) are then reduced to give piperidines of Formula (I) in the presence of a reducing agent and an inert solvent.

Scheme IV

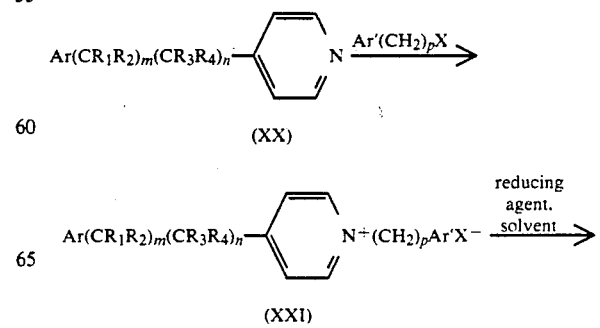

-continued
Scheme IV

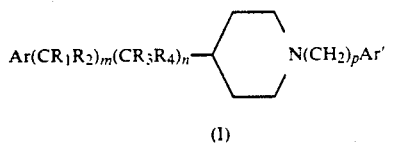

Reducing agents include molecular hydrogen in the presence of a noble metal catalyst such as palladium on carbon, platinum on carbon, platinum dioxide. Other reducing agents include alkali metal borohydrides (preferably sodium borohydride), diborane, alkali metal aluminum hydrides, trialkyltin hydrides, or diimide. Those skilled in the art will recognize that some of the above reagents will only partially reduce the pyridine ring to give tetrahydropyridine intermediates. It is therefore necessary to use combinations of the above reducing agents or to use these agents sequentially to afford the desired piperidine products. Inert solvents include those defined for Scheme III. The choice of reagents and solvents follow the examples taught by the March reference cited above (pp. 691–707, 1093–1120) and R. L. Augustine (*Catalytic Hydrogenation*, New York:Marcel Dekker, 1965).

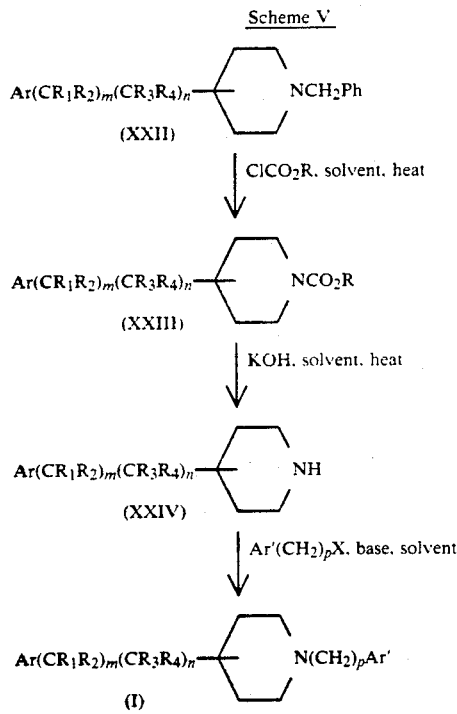

The compounds of this invention may also be prepared according to Scheme V. N-Benzylpiperidines of Formula (XXII) are converted to the corresponding carbamates (XXIII) by reaction with an alkylchloroformate of 2 to 20 carbons in an inert solvent such as benzene, toluene or tetrahydrofuran at temperatures ranging from about 25° to 120° C.

Intermediates (XXIII) may be hydrolyzed to piperidines (XXIV) using an alkali metal hydroxide in water. Water miscible solvents may be used as cosolvents in cases where solubility is a problem. These water miscible solvents include hydroxyhydrocarbons of 1 to 10 carbons (preferably methanol or ethanol), 1,4-dioxane or tetrahydrofuran. Reaction temperatures range from about 25° to 150° C. The resulting piperidines (XXIV) may be reacted with a compound of the Formula $Ar'(CH_2)_pX$ in the presence of a base and an inert solvent to yield compounds of Formula (I). X is a leaving group as defined for Scheme IV. The same bases and inert solvents defined for Scheme IV may be employed here. In addition, bases may include alkali metal hydroxides, alkali metal carbonates, alkaline earth metal carbonates or alkali metal hydrides.

EXPERIMENTAL SECTION

Analytical data were recorded for the compounds described below using the following general procedures. Infrared spectra were recorded on a Perkin-Elmer Model 1600 FT-IR spectrometer; absorbances are recorded in $cm^{-1}$ and intensities are denoted s (strong), m (moderate) and w (weak). Proton NMR spectra were recorded on an IBM-Bruker model 200 FT-NMR (200 MHz); chemical shifts were recorded in ppm ($\delta$) from an internal tetramethylsilane standard in deuterochloroform and coupling constants (J) are reported in Hz. Mass spectra (MS) were recorded on Finnegan MAT spectrometer. Melting points were recorded on a Buchi model 510 melting point apparatus and are uncorrected. Boiling points are uncorrected. Parts and percentages are by weight unless otherwise specified.

Reagents were purchased from commercial sources and, where necessary, purified prior to use according to the general procedures outlined by D. D. Perrin and W. L. F. Armarego, *Purification of Laboratory Chemicals*. 2nd ed., (New York:Pergamon Press, 1988). Chromatography was performed on silica gel using the solvent systems indicated below.

EXAMPLE 1

Part A: 1-Benzyl-4-(methoxymethylidene) piperidine

A solution of di-isopropylamine (11.1 g, 15.4 mL, 110 mmol) in anhydrous tetrahydrofuran (100 mL) was cooled to 0° C. under a nitrogen atmosphere. A solution of n-butyl lithium in hexanes (2.5 M, 44 mL, 110 mmol) was added dropwise with stirring. The pale yellow solution was stirred for 15 minutes at 0° C., then transferred via cannula to a suspension of methoxymethyltriphenylphosphonium chloride (37.7 g, 110 mmol) in dry tetrahydrofuran (300 mL) stirred at −20° C. After 30 minutes, the reaction mixture was cooled to −40° C. and a solution of 1-benzylpiperid-4-one (18.9 g, 18.5 mL, 100 mmol) in anhydrous tetrahydrofuran (100 mL) was added dropwise over 15 minutes. The reaction mixture was warmed gradually to ambient temperature over 23 h. The reaction mixture was then poured onto water, mixed and extracted three times with ethyl acetate. The combined organic layers were dried over magnesium sulfate and filtered; solvent was removed in vacuo. Column chromatography (ethyl acetate) gave starting piperidine ($R_f=0.7$, 0.5 g) and the product ($R_f=0.51$, 11.6 g), an orange-yellow liquid: $^1$HNMR:7.4–7.25(m,5H), 5.8(s,1H), 3.5(s,2H), 3.45(s,3H), 2.5–2.3(m,5H), 2.05(t,2H,J=7); MS:217.

Part B: 1-Benzyl-4-formylpiperidine

Method A

A mixture of 1-benzyl-4-(methoxymethylidene)-piperidine (11.6 g, 63.4 mmol), a 4N hydrochloric acid solution (100 mL) and tetrahydrofuran (40 mL) was stirred at ambient temperature for 16 h. Solid potassium carbonate was added portionwise until pH=9. The mixture was diluted twofold with water and extracted three times with ethyl acetate. The combined organic layers were dried over magnesium sulfate and filtered. Solvent was removed in vacuo to give a clear pale yellow liquid (10.0 g):$^1$HNMR:9.65(s,1H), 7.4-7.3(m,5H), 3.5(s,2H), 2.9-2.75(m,2H), 2.4-1.6(m,7H); MS:203.

Part B
Method B

A solution of oxalyl chloride (3 g, 2.06 mL, 23.6 mmol) in dichloromethane (100 mL) was cooled to −78° C. with stirring under a nitrogen atmosphere. A solution of dimethyl sulfoxide (3.7 g, 3.36 mL, 47.3 mmol) in dichloromethane (100 mL) was added dropwise. The reaction mixture was stirred for 15 minutes. A solution of 1-benzyl-4-hydroxymethylpiperidine (3.6 g, 17.6 mmol) in dichloromethane (100 mL) was added dropwise; then the reaction mixture was stirred at −65° to −60° C. for 15 minutes. The reaction mixture was cooled to −78° C. and triethylamine (6.83 g, 9.41 mL, 67.5 mmol) was added in one portion. The reaction mixture was warmed to ambient temperature over 6h, then it was poured onto water, mixed and extracted three times with ether. The combined organic layers were dried over magnesium sulfate and filtered. Solvent was removed in vacuo. Column chromatography (ethyl acetate) gave the product, a clear pale yellow liquid (2.64 g), which was identical in all respects to the product obtained in Part B; Method A.

Part C:
1-Benzyl-4-(2′-4″-fluorophenyl)-1-hydroxyethyl)piperidine

Magnesium mesh (1.21 g, 50 mmol) was suspended in anhydrous tetrahydrofuran (100 mL) with stirring under a nitrogen atmosphere. A solution of 4-fluorobenzylchloride (7.23 g, 6.0 mL, 50 mmol) in dry tetrahydrofuran (50 mL) was added dropwise over 5 minutes. The reaction mixture was stirred at reflux temperature for 30 minutes. A solution of 1-benzyl-4-formyl-piperidine (5.0 g, 24.6 mmol) in dry tetrahydrofuran (50 mL) was added dropwise. The resulting mixture was stirred at reflux temperature for 14.5 hours. After being cooled to ambient temperature, the mixture was poured onto water, mixed and extracted three times with ethyl acetate. The combined organic layers were dried over magnesium sulfate and filtered. Solvent was removed in vacuo to give a yellow oil. Column chromatography gave the product, a clear yellow oil (R$^f$=0.12, 5.74 g): $^1$HNMR:7.35-6.85(m, 9H), 4.60-4.45(m,1H), 4.50(s,2H), 3.0-2.45(m,4H), 200-1.6(m,7H); IR (neat):3412(s,br), 3063(m), 3029(m), 2938(s), 2803 (m), 1601(s), 1510(s), 1467(s), 1453(s); MS:313.

EXAMPLES 2 to 37

Examples 2 to 37 were or could be prepared by the procedure described for Example 1 using the appropriate aryl methyl magnesium halide and a 4-formyl-1-aralkyl piperidine.

TABLE 1

Structure: R$_1$—phenyl—CH$_2$—CH(OH)—piperidine(N—CH$_2$—phenyl—R$_2$)

| Example | R$^1$ | R$^2$ | m.p. (°C.) |
|---|---|---|---|
| 1 | 4-F | H | oil$^{(a)}$ |
| 2 | 4-Cl | H | |
| 3 | 4-OTBDMS$^{(b)}$ | H | |
| 4 | 4-C$_2$H$_5$ | H | |
| 5 | 4-OCH$_3$ | H | 84-86$^{(c)}$ |
| 6 | 4-NO$_2$ | H | |
| 7 | 4-N(CH$_3$)$_2$ | H | |
| 8 | 4-NHAc | H | |
| 9 | 4-SCH$_3$ | H | |
| 10 | 4-t-Bu | H | 69-70$^{(d)}$ |
| 11 | 4-SO$_2$CH$_3$ | H | |
| 12 | 4-CF$_3$ | H | |
| 13 | 4-CN | H | |
| 14 | 4-CH(OCH$_2$CH$_2$O) | H | |
| 15 | 4-Pr | H | |
| 16 | 4-Bu | H | |
| 17 | 4-CH$_3$ | H | |
| 18 | 3-F | H | |
| 19 | 2-F | H | |
| 20 | 3-OTBDMS$^{(b)}$ | H | |
| 21 | 3-C$_2$H$_5$ | H | |
| 22 | 3-OCH$_3$ | H | |
| 23 | 3-NO$_2$ | H | |
| 24 | 3-SCH$_3$ | H | |
| 25 | 3-CN | H | |
| 26 | 3,4-F$_2$ | H | |
| 27 | 3,4-Cl$_2$ | H | |
| 28 | 3,4-(CH$_3$O)$_2$ | H | |
| 29 | 3-F, 4-OH | H | |
| 30 | 3-OH, 4-F | H | |
| 31 | 4-F | 4-F | |
| 32 | 4-F | 4-Cl | |
| 33 | 4-F | 4-OCH$_3$ | |
| 34 | 4-F | 4-OTBDMS$^{(b)}$ | |
| 35 | 4-F | 4-OH | |
| 36 | 4-F | 4-NHAc | |
| 37 | 4-F | 4-N(CH$_3$)$_2$ | |

Footnotes for Table 1:
$^{(a)}$$^1$H-NMR: 7.35-6.85(m, 9H), 4.6-4.45(m, 1H), 4.50(s, 2H), 3.0-2.45(m, 4H), 2.0-1.6(m, 7H); MS:313.
$^{(b)}$TBDMS = t-butyldimethylsilyloxy
$^{(c)}$mp 84-86°; $^1$H-NMR: 7.4-7.25(m, 5H), 7.15(d, 2H, J=2), 6.9(d, 2H, J=7), 3.8(s, 3H), 3.6-3.5(m, 1H), 3.1-2.75(m, 3H), 2.55(dd, 1H, J=9, 7), 2.15-1.4(m, 9H); HR-MS: Calcd for C$_{21}$H$_{27}$NO$_2$: 325.2042; Found: 325.2019.
$^{(d)}$Anal.: Calcd for C$_{24}$H$_{33}$NO: C, 82.00, H, 9.46, N, 3.98; Found: C, 81.75, H, 9.32, N, 3.96.

EXAMPLE 38

1-Benzyl-4-(2′(4″-Fluorophenyl)-1-hydroxyethyl) Piperidine, Hydrochloride Salt 1-Benzyl-4-(2′(4″-fluorophenyl)hydroxyethyl) piperidine (1.0 g, 3.2 mmol) from Example 1, was dissolved in diethyl ether with stirring. Anhydrous hydrogen chloride was bubbled through the solution; the precipitate was collected by filtration, triturated with fresh ether and filtered again. Drying in vacuo afforded a white powder (780 mg):mp-64°-66° C.; $^1$H-NMR(DMSO-d6):11.1-10.8(m,1H), 7.75-7.0(m,9H), 5.9-5.75(m,1H), 4.4-4.25(m,2H), 3.5-2.5(m,8H); 2.0-1.3(m,3H); Anal.-:Calcd for C$_{20}$H$_{24}$FNO-HCl-0.25H$_2$O:C,67.12, H,7.04, N,3.91; Found: C,67.43, 67.40, H,7.34, 7.41, N,4.17, 4.01.

EXAMPLES 39-42

Examples 39-42 were or could be prepared by the procedure described for Example 38 using the appropriate acid and the appropriate solvent.

TABLE 2

[Structure: R1-phenyl-CH(OH)-piperidine-N-CH2-phenyl-R2 · HX]

| Example | R¹ | R² | HX |
|---------|-----|-----|------|
| 38 | 4-F | H | HCl[a] |
| 39 | 4-CH₃O | H | HCl |
| 40 | 4-NO₂ | H | HCl |
| 41 | 4-CF₃ | H | HCl |
| 42 | H | H | HCl[b] |

NOTES:
[a] Contained 0.25 H₂O.
[b] mp = 60° C. (dec.); Anal.: Calcd for C₂₀H₂₅NO.HCl.0.04 H₂O: C, 70.84, H, 7.66, N, 4.13; Found: C, 70.79, H, 7.88, N, 4.12.

EXAMPLE 43

1-Benzyl-4-(2'(4''-fluorophenyl)acetyl)piperidine

A solution of oxalyl chloride (1.25 g, 0.17 mL, 2.6 mmol) in dichloromethane (5 mL) was cooled to −78°60 C. in a flame dried flask under a nitrogen atmosphere with stirring. A solution of dimethylsulfoxide (0.41 g, 0.37 mL, 5.2 mmol) in dichloromethane (5 mL) was added dropwise; then the reaction mixture was stirred for 15 minutes. A solution of 1-benzyl-4-(2'-(4''-fluorophenyl)hydroxyethyl)piperidine (0.6 g, 2 mmol) in dichloromethane was added dropwise, then the reaction mixture was stirred at −65° to −60° C. for 15 minutes. The mixture was then cooled to −78° C. and triethylamine (0.73 g, 1.0 mL, 7.2 mmol) was added in one portion. The reaction mixture was stirred while being warmed gradually to ambient temperature. After 3 hours, the reaction mixture was poured onto water (100 mL), mixed and extracted three times with ether. The combined organic layers were dried over magnesium sulfate filtered and concentrated in vacuo. Column chromatography (ethyl acetate) gave an oil (588 mg, Rf=0.2):¹H-NMR:7.4-6.9(m,9H), 4.65(s,2H), 4.5(s,2H), 3.0-2.9(m,2H), 2.5-2.35(m,1H), 2.1-1.6(m,8H); HR-MS:Calcd for C₂₀H₂₂FNO:311.1700; Found:311.1693.

EXAMPLES 44 to 67

Examples 44 to 67 were or could be prepared according to the procedure described for Example 43 using the appropriate 1-aralkyl-4-arylhydroxyethyl piperidine.

TABLE 3

[Structure: R1-phenyl-CH2-C(O)-piperidine-N-CH2-phenyl-R2]

| Example | R¹ | R² | m.p. (°C.) |
|---------|-----|-----|------------|
| 43 | 4-F | H | oil[a] |
| 44 | 4-Cl | H | |
| 45 | 4-OTBDMS | H | |
| 46 | 4-C₂H₅ | H | |
| 47 | 4-OCH₃ | H | |

TABLE 3-continued

| Example | R¹ | R² | m.p. (°C.) |
|---------|-----|-----|------------|
| 48 | 4-NO₂ | H | |
| 49 | 4-NMe₂ | H | |
| 50 | 4-SCH₃ | H | |
| 51 | 4-t-Bu | H | |
| 52 | 4-SO₂CH₃ | H | |
| 53 | 4-CN | H | |
| 54 | H | H | |
| 55 | 3,4-F₂ | H | |
| 56 | 3,4-Cl₂ | H | |
| 57 | 4-F | 4-F | |
| 58 | 4-F | 3-F | |
| 59 | 4-F | 3-OCH₃ | |
| 60 | 4-F | 3-OH | |
| 61 | 4-F | 4-OCH₃ | |
| 62 | 4-F | 4-OTBDMS | |
| 63 | 4-F | 4-OH | |
| 64 | 4-F | 4-N(CH₃)₂ | |
| 65 | 4-F | 4-Cl | |
| 66 | 4-F | 3-Cl | |
| 67 | 4-CF₃ | H | |

NOTES:
[a] ¹H-NMR: 7.4-6.9(m, 9H), 4.65(s, 2H), 4.5(s, 2H), 3.0-2.9(m, 2H), 2.5-2.35(m, 1H), 2.1-1.6(m, 8H); HR-MS: Calcd for C₂₀H₂₂FNO: 311.1700; Found: 311.1693.

EXAMPLE 68

1-Benzyl-4-(2'-(4''-fluorophenyl)acetyl) piperidine, maleate salt

The free base of Example 43 was dissolved in ether (5 mL) with stirring. A saturated solution of maleic acid in ether (10 mL) was added. The white precipitate was filtered and washed with copious amounts of ether. Drying in vacuo afforded a white powder (521 mg):mp 132°-134° C.; ¹H-NMR .(DMSO-d6):7.5(s,5H), 7.3-7.1(m,4H), 6.05(s,2H), 4.3(s,2H), 3.95(s,2H), 3.6-2.7(m,10H), 2.15-1.5(m,4H); Anal.:Calcd for C₂₀H₂₂FNO·C₄H₄O₄-0.75 H₂O:C,65.36, H,6.29, N,3.18; Found:C,65.53, 65.60, M,5.93, 5.90, N,3.20, 3.21.

EXAMPLE 69 to 72

Examples 69 to 72 were or could be prepared by the procedure for Example 68 using the appropriate acid and the appropriate solvent.

TABLE 4

[Structure: R1-phenyl-CH2-C(O)-piperidine-N-CH2-phenyl-R2 · HX]

| Example | R¹ | R² | HX |
|---------|-----|-----|------|
| 68 | 4-F | H | Maleate[a] |
| 69 | 4-CH₃O | H | Maleate |
| 70 | 4-NO₂ | H | Maleate |
| 71 | 4-CF₃ | H | Maleate |
| 72 | H | H | Maleate[b] |

NOTES
[a] contained 0.75 H₂O, mp 132-134° C.
[b] mp 116-118; Anal.: Calcd for C₂₀H₂₃NO.C₄H₄O₄: C, 70.40, H, 6.65, N, 3.42; Found: C, 70.12, H, 6.44, N, 2.26.

EXAMPLE 73

Part A: 1-Benzyl-4(2'-methoxyethenyl)piperidine

A solution of di-isopropylamine (4.38 g, 6.1 mL, 43.3 mmol) in anhydrous tetrahydrofuran (50 mL) was cooled to 0° C. with stirring. A solution of n-butyl lithium in hexanes (2.4 M, 17.3 mL, 43.3 mmol) was added dropwise; the resulting solution was stirred for 15 minutes. The reaction mixture was transferred via cannula to a suspension of methoxymethyl triphenyl phosphonium chloride (14.9 g, 43.3 mmol) in anhydrous tetrahydrofuran (100 mL), stirred at $-20°$ C. The reaction mixture was stirred at $-20°$ C. for 35 minutes, then it was cooled to $-40°$ C. A solution of 1-benzyl-4-formylpiperidine (8 g, 39.4 mmol) in anhydrous tetrahydrofuran (50 mL) was added dropwise. The reaction mixture was warmed gradually to ambient temperature over 21 hours, then it was poured onto water (500 mL) mixed and extracted three times with ethyl acetate (500 mL). The combined organic layers were dried over magnesium sulfate, treated with decolorizing charcoal and filtered through Celite ®. Solvent was removed in vacuo to give an orange oil. Column chromatography (ethyl acetate) gave the product as a mixture of E- and Z- isomers (Rf=0.41, 5.06 g):$^1$H-NMR:7.4-7.2(m,5H), 6.3(d,0.6H,J=13), 5.8(d,0.4H,J=6), 4.65(dd,0.6H,J=13,6), 4.2(dd,0.4H,J=6,5), 3.5(s,1.2H), 3.45(s,1.8H), 2.9-2.7(m,2H), 2.5-2.3(m,1H), 2.1-1.3(m,7H); HR-MS:Calcd for $C_{15}H_{21}NO$:231.1623; Found:231.1633.

Part B; 1-Benzyl-4-formylmethyl piperidine

Method A

A mixture of 1-benzyl-4-(2'-methoxyethenyl)piperidine (5.0 g, 21.6 mmol), a 4 N Hydrochloric acid solution (50 mL) and tetrahydrofuran was stirred at room temperature for 17 hours. The solution was carefully neutralized with solid potassium carbonate. The layers were separated. The aqueous layer was extracted three times with ethyl acetate. The combined organic layers were dried over magnesium sulfate, filtered and concentrated in vacuo. Column chromatography (ethyl acetate:hexanes, 1:1) gave a clear pale yellow liquid (Rf=0.1, 3.65 g):$^1$H-NMR:9.7(t,1H,J=1), 7.45-7.2(m,5H), 3.5(s,2H), 2.95-2.75(m,2H), 2.35(dd,2H,J=7,1), 2.1-1.6(m,4H), 1.45-1.2(m,2H); IR (neat:3085(m), 3062(m), 3057(m), 2920(s), 2803(s), 2757(s), 2723(s), 1724(s), 1603(w), 1495(m) 1467(m), 1454(m); HR-MS:Calcd for $C_{14}H_{19}NO$:217.1466, Found:217.1460.

Method B

A solution of 1-benzylpiperidine-4-acetonitrile (45 g, 210 mmol) in toluene (500 mL) was stirred under a nitrogen atmosphere at ambient temperature. A solution of di-isobutylaluminum hydride in toluene (1.5 M, 166 mL, 250 mmol) was added dropwise. The reaction mixture was heated to reflux temperature and stirred for 24 hours. After cooling to room temperature, a saturated ammonium chloride solution (400 mL) was added gradually. The mixture was poured onto 500 mL 1 N sodium hydroxide solution and mixed. The layers were separated. The aqueous layer was extracted twice with toluene. The combined organic layers were dried over magnesium sulfate, filtered and concentrated in vacuo. Column chromatography (ethyl acetate) gave the starting nitrile (Rf=0.33, 14.7 g) and the product (Rf=0.25, 10.1 g), which was identical in all respects to the product from Part B; Method A.

Part C: 1-Benzyl-4-(2'-(4''-Fluorophenyl)-2'-hydroxyethyl)-piperidine

A mixture of a solution of 4-fluorophenyl-magnesium bromide in ether (2 M, 12.5 mL, 25 mmol) and anhydrous tetrahydrofuran (25 mL) was stirred at ambient temperature under a nitrogen atmosphere. A solution of 1-benzyl-4-formylmethylpiperidine (3.6 g, 16.6 mmol) in anhydrous tetrahydrofuran (25 mL) was added dropwise. The reaction mixture was stirred for 19 hours, then it was poured onto a saturated ammonium chloride solution, mixed and extracted three times with ethyl acetate (50 mL). The combined organic layers were dried over magnesium sulfate, filtered and concentrated in vacuo. Column chromatography (ethyl acetate:hexanes:1:1) gave the product, a pale yellow solid (Rf=0.08, 2.7 g):mp=84°–86° C.; $^1$H-NMR:7.4-7.25(m,7H), 7.0(t,2H,J=8), 4.7(dd,1H,J=8,6), 3.45(s,2H), 2.9-2.75(m,2H), 2.1-1.2(m,10H); HR-MS:Calcd for $C_{20}H_{24}FNO$:313.1842; Found:313.1862.

EXAMPLES 74 TO 103

Examples 74 to 103 have or can be prepared by the procedure described for Example 73 using the appropriate aryl magnesium halide or aryl lithium and a 1-aralkyl-4-formylmethylpiperidine.

TABLE 5

| Example | R$^1$ | R$^2$ | m.p. (°C.) |
|---|---|---|---|
| 73 | 4-F | H | 84–86$^{(a)}$ |
| 74 | 4-Cl | H | |
| 75 | 4-OTBDMS$^{(b)}$ | H | $^{(c)}$ |
| 76 | 4-Ph | H | 126–127$^{(d)}$ |
| 77 | 4-OCH$_3$ | H | $^{(e)}$ |
| 78 | 4-NO$_2$ | H | |
| 79 | 4-N(CH$_3$)$_2$ | H | |
| 80 | 4-SCH$_3$ | H | 113–114$^{(f)}$ |
| 81 | 4-CN | H | |
| 82 | 4-CF$_3$ | H | $^{(g)}$ |
| 83 | 3-F | H | |
| 84 | 2-F | H | |
| 85 | 3-OTBDMS$^{(b)}$ | H | |
| 86 | 4-TBDMSOCH$_2$ | H | 61–62$^{(h)}$ |
| 87 | 3-OCH$_3$ | H | |
| 88 | 4-SCH$_3$ | H | |
| 89 | 4-PhO | H | 90–91$^{(i)}$ |
| 90 | 4-F | 4-F | |
| 91 | 4-F | 4-Cl | |
| 92 | 4-F | 4-NO$_2$ | |
| 93 | 4-F | 4-N(CH$_3$)$_2$ | |
| 94 | 4-F | 4-OCH$_3$ | |
| 95 | 4-F | 4-OH | |
| 96 | 4-F | 4-OTBDMS$^{(b)}$ | |
| 97 | 4-F | 3-F | |
| 98 | 4-F | 3-Cl | |
| 99 | 4-F | 3-OCH$_3$ | |
| 100 | 4-F | 3-OH | |
| 101 | 4-F | 3-OTBDMS$^{(b)}$ | |
| 102 | 4-F | 3-NO$_2$ | |

TABLE 5-continued

| 103 | 4-F | 4-CF₃ |

[a]HR-MS: Calcd for C₂₀H₂₄FNO: 313.1835; Found: 313.1839; H-NMR: 7.33-7.23(m, 7H), 7.06-6.97(m, 2H), 4.73(dd, 1H, J=9.5), 3.47(s, 2H), 2.86(br d, 2H, J=9), 2.34(s, 1H), 1.97-1.25(m, 10H).
[b]TBDMS=t-butyldimethylsilyloxy.
[c]¹H-NMR (CDCl₃, 300MHz): 7.3-7.1(m, 7H), 6.8(d, 2H, J=8), 3.4(s, 2H), 2.8(d, 2H, J=11), 2.1(s, 2H), 1.2-1.9(m, 9H), 1.0(s, 9H), 0.2(s, 6H); HRMS: Calcd for C₂₆H₃₀NO₂Si: 425.2750. Found: 425.2756.
[d]Anal.: Calcd for C₂₆H₂₉NO: C, 84.06, H, 7.87, N, 3.77; Found: C, 83.89, H, 7.89, N, 3.64.
[e]¹H-NMR (CDCl₃, 300MHz): 7.4-7.2(m, 7H), 6.8(d, 2H, J=8), 4.7(m, 1H), 3.8(s, 3H), 3.4(s, 2H), 2.8(d, 2H, J=10), 2.2(br, s, 1H), 2.0-1.2(m, 9H); MS: 325.
[f]Anal.: Calcd for C₂₁H₂₇NOS: C, 73.86, H, 7.97, N, 4.10, S, 9.39; Found: C, 73.87, H, 7.99, N, 4.04, S, 9.37.
[g]¹H-NMR (CDCl₃, 300MHz): 7.6-7.2(m, 9H), 4.8(dd, 1H, J=8.4), 3.5(s, 2H), 2.9(m, 2H), 1.9(t, 2H, J=11), 1.8-1.2(m, 7H); MS=363.
[h]Anal.: Calcd for C₂₇H₄₁NO₂Si: C, 73.75, H, 9.40, N, 3.19; Found: C, 73.55, H, 9.14, N, 3.15.
[i]Anal.: Calcd for C₂₆H₂₉NO₂: C, 80.59, H, 7.54, N, 3.61; Found: C, 80.42, H, 7.57, N, 3.60.

EXAMPLE 104

1Benzyl-4-(2'-(4''-fluorophenyl)-2'-hydroxyethyl)-piperidine, hydrochloride salt A solution of hydrogen chloride in ether (1M, 30 mL) was added dropwise to a solution of 1-benzyl-4-(2'-fluorophenyl-2'-hydroxyethy) piperidine (2.2 g, 7 mmol) from Example 73, in ether (100 mL) with vigorous stirring. The white precipitate was filtered and washed with copious amounts of ether. Drying in vacuo afforded a white powder (2.3 g):mp 188°-190° C.; ¹H-NMR (DMSO-d₆):11.0-10.7(m,1H), 7.75-7.0(m,9H), 5.4(d,1H,J=1), 4.65-4.55(m,1H), 4.45-4.25(m,2H), 3.5-2.5(m,5H), 2.0-1.3(m,6H); Anal.:Calcd for C₂₀H₂₄FNO-HCl:C,68.66, H,7.20, N,4.00; Cl,10.13; Found:C,68.24, H,7.11, N,3.91, Cl,10.00.

EXAMPLES 105 TO 108

Examples 105 to 108 were or could be prepared via the procedure described for Example 104 using the appropriate acid and the appropriate solvent.

TABLE 6

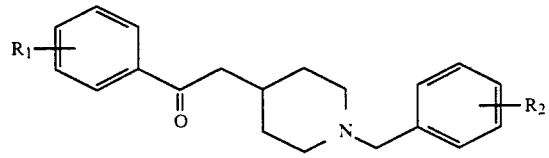

| Example | R¹ | R² | HX |
|---|---|---|---|
| 104 | 4-F | H | HCl[a] |
| 105 | H | H | HCl |
| 106 | 4-CH₃O | H | HCl[b] |
| 107 | 4-NO₂ | H | HCl |
| 108 | 4-CF₃ | H | HCl[c] |

Notes for Table 6:
[a]mp 189-190° C.; Anal.: Calcd for C₂₀H₂₄FNO.HCl: C, 68.66, H, 7.20, N, 4.00, Cl, 10.13; Found: C, 68.24, H, 7.11, N, 3.91, Cl, 10.00.
[b]mp 170-171° C.; Anal.: Calcd for C₂₁H₂₇NO₂.HCl: C, 69.69, H, 7.80, N, 3.87, Cl, 9.80; Found: C, 69.52, H, 7.91, N, 3.82, Cl, 9.37.
[c]mp 249-250° C.; Anal.: Calcd for C₂₁H₂₄F₃NO.HCl: C, 63.08, H, 6.30, N, 3.50, Cl, 8.87; Found: C, 62.83, H, 6.26, N, 3.37, Cl, 9.10.

EXAMPLE 109

1-Benzyl-4-(2'-4''-fluorophenyl)-2-oxoethyl)piperidine

A solution of oxalyl chloride (0.21 g, 0.14 mL, 2.2 mmol) in dichloromethane (5 mL) was cooled to −78° C. with stirring under a nitrogen atmosphere. A solution of dimethyl sulfoxide (0.33 g, 0.3 mL, 4.4 mmol) in dichloromethane (5 mL) was added dropwise. The reaction mixture was stirred at −79° C. for 15 minutes. A solution of 1-benzyl-4-(2'-(4''-fluorophenyl)-2-hydroxyethyl)piperidine (0.5 g, 1.6 mmol) in dichloromethane (5 mL) was added dropwise. The reaction mixture was then stirred for 15 minutes, then triethylamine (0.59 g, 0.8 mL, 5.78 mmol) was added in one portion. The reaction mixture was warmed gradually to ambient temperature with stirring over 25 hours, then it was poured onto water (50 mL), mixed and extracted three times with ether. The combined organic layers were dried over magnesium sulfate, filtered and concentrated in vacuo. Column chromatography (ethyl acetate) gave the product, a pale yellow solid (R_f=0.25, 186 mg):¹H-NMR:7.95(dd,2H,J=8,6), 7.35-7.25(m,5H), 7.15(t,2H,J=6), 3.5(s,2H), 2.95-2.8(m,4H), 2.1-1.9(m,3H), 1.8-1.7(m,2H), 1.5-1.25(m,2H); HR-MS:Calcd for C₂₀H₂₂FNO:311.1685; Found:311.1687.

EXAMPLES 110 TO 133

Examples 110 to 133 were or could be prepared via the procedure described for Example 109 using the appropriate 1-aralkyl-4-(2-aryl-2-hydroxyethyl)piperidine.

TABLE 7

| Example | R¹ | R² | m.p. (°C.) |
|---|---|---|---|
| 109 | 4-F | H | [a] |
| 110 | 4-Cl | H | |
| 111 | 4-OTBDMS[b] | H | |
| 112 | 4-Ph | H | 121-122[b] |
| 113 | 4-OCH₃ | H | 59-60[c] |
| 114 | 4-NO₂ | H | |
| 115 | 4-N(CH₃)₂ | H | |
| 116 | 4-SCH₃ | H | 98-99[d] |
| 117 | 4-PhO | H | 54-55[e] |
| 118 | 4-TBDMSOCH₂ | H | |
| 119 | 4-CN | H | |
| 120 | 4-Et | H | |
| 121 | 3,4-F₂ | H | |
| 122 | 3,4-Cl₂ | H | |
| 123 | 3,4-(CH₃O)₂ | H | |
| 124 | 4-F | 4-F | |
| 125 | 4-F | 3-F | |
| 126 | 4-F | 4-Cl | |
| 127 | 4-F | 3-Cl | |
| 128 | 4-F | 4-OH | |
| 129 | 4-F | 4-OTBDMS | |
| 130 | 4-F | 4-N(CH₃)₂ | |
| 131 | 4-F | 3-OCH₃ | |
| 132 | 4-F | 4-OCH₃ | |
| 133 | 4-CF₃ | H | 64-65[f] |

Footnotes for Table 7:
[a]¹H-NMR: 7.95(dd, 2H, J=8,6), 7.35-7.25(m, 5H), 7.15(t, 2H, J=6), 3.5(s, 2H), 2.95-2.8(m, 4H), 2.1-1.9(m, 3H), 1.8-1.7(m, 2H) 1.5-1.25(m, 2H).
[b]TBDMS=t-butyldimethylsilyloxy
[c]Anal.: Calcd for C₂₆H₂₇NO: C, 84.51, H, 7.37, N, 3.79; Found: C, 84.30, H, 7.18, N, 3.80.
[d]Anal.: Calcd for C₂₁H₂₅NO₂: C, 77.98, H, 7.79, N, 4.33; Found: C, 77.73, H, 7.81, N, 4.03.
[e]Anal.: Calcd for C₂₁H₂₅NOS: C, 74.29, H, 7.42, N, 4.13, S, 9.44; Found: C, 74.43, H, 7.36, N, 4.07, S, 9.44.
[f]Anal.: Calcd for C₂₆H₂₇NO₂: C, 81.01, H, 7.06, N, 3.63; Found: C, 80.76, H, 6.90, N, 3.54.
[g]Anal.: Calcd for C₂₁H₂₂F₃NO.0.25H₂O: C, 68.93, H, 6.19, N, 3.83, F, 15.58; Found: C, 68.65, 68.57, H, 5.68, 5.94, N, 3.67, 3.71, F, 16.02.

EXAMPLE 134

1-Benzyl-4-(2'-(4''-Fluorophenyl)-2'-oxoethyl)piperidine, maleate salt

A saturated solution of maleic acid in ether (20 mL) was added to a solution of 1-benzyl-4-(2-(4''-fluorophenyl)-2'-oxoethyl)piperidine (186 mg. 0.59 mmol) in ether (10 mL) with stirring. The white precipitate was filtered and washed with copious amounts of ether. Drying in vacuo afforded a white powder (284 mg):mp 106°–108° C.; $^1$H-NMR:12.2-12.0(m,1H), 8.0(dd,2H,J=8,6), 7.5-7.35(m,5H), 7.15(t,2H,J=8), 6.4(s,2H), 4.2(s,2H), 3.65-3.4(m,2H), 2.95(d,2H,J=6), 2.9-2.7(m,2H). 2.4-1.6(m,4H); Anal.:Calcd for $C_{20}H_{22}FNO \cdot C_4H_4O_4 \cdot 0.25H_2O$:C,66.73, H,6.18, N,3.24; Found:C,66.50, H,5.97, N,3.10.

EXAMPLES 135 TO 138

Examples 135 to 138 were or could be prepared using the method described for Example 134 employing the appropriate acid and the appropriate solvent.

TABLE 8

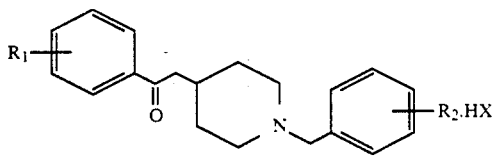

| Example | R$^1$ | R$^2$ | HX |
|---|---|---|---|
| 134 | 4-F | H | Maleate$^{(a)}$ |
| 135 | H | H | Maleate |
| 136 | 4-CH$_3$O | H | Maleate |
| 137 | 4-NO$_2$ | H | Maleate |
| 138 | 4-CF$_3$ | H | Maleate |

NOTES:
$^{(a)}$Contained 0.25 H$_2$O. mp 106-108° C.

EXAMPLES 139 TO 147

Examples 139 to 147 were or could be prepared by the procedure described for Example 1 using the appropriate arylmethyl magnesium halide and a 4-formyl-1-aralkyl-piperidine.

TABLE 9

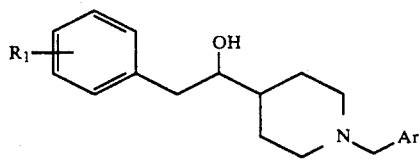

| Example | R1 | Ar |
|---|---|---|
| 139 | 4-F | 4-pyridyl |
| 140 | 4-F | 3-pyridyl |
| 141 | 4-F | 2-pyridyl |
| 142 | 4-F | 2-pyrimidyl |
| 143 | 4-F | 4-pyrimidyl |
| 144 | 4-F | 2-quinolinyl |
| 145 | 4-F | 4-quinolinyl |
| 146 | 4-F | 2-naphthyl |
| 147 | 4-F | 1-naphthyl |

EXAMPLES 148 TO 156

Examples 148 to 156 were or could be prepared via the procedure described for Example 43 using the appropriate 1-aralkyl-4-arylhydroxyethyl piperidine.

TABLE 10

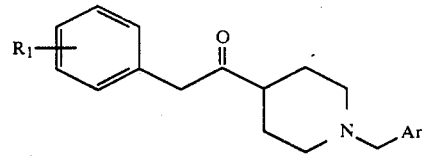

| Example | R1 | Ar |
|---|---|---|
| 148 | 4-F | 4-pyridyl |
| 149 | 4-F | 3-pyridyl |
| 150 | 4-F | 2-pyridyl |
| 151 | 4-F | 2-pyrimidyl |
| 152 | 4-F | 4-pyrimidyl |
| 153 | 4-F | 2-quinolinyl |
| 154 | 4-F | 4-quinolinyl |
| 155 | 4-F | 2-naphthyl |
| 156 | 4-F | 1-naphthyl |

EXAMPLES 157 TO 165

Examples 157 to 165 were or could be prepared via the procedure described for Example 73 using the appropriate aryl magnesium halide or aryl lithium and a 1-aralkyl-4-formylmethyl piperidine.

TABLE 11

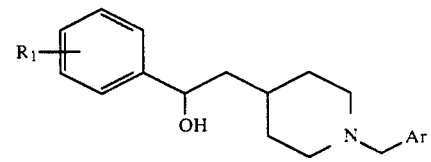

| Example | R1 | Ar |
|---|---|---|
| 157 | 4-F | 4-pyridyl |
| 158 | 4-F | 3-pyridyl |
| 159 | 4-F | 2-pyridyl |
| 160 | 4-F | 2-pyrimidyl |
| 161 | 4-F | 4-pyrimidyl |
| 162 | 4-F | 2-quinolinyl |
| 163 | 4-F | 4-quinolinyl |
| 164 | 4-F | 2-naphthyl |
| 165 | 4-F | 1-naphthyl |

EXAMPLES 166 TO 174

Examples 166 to 174 were or could be prepared via the procedure described for Example 109 using the appropriate 1-aralkyl-4-(2'-aryl-2'-hydroxyethyl)piperidine.

TABLE 12

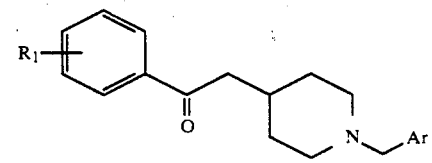

| Example | R1 | Ar |
|---|---|---|
| 166 | 4-F | 4-pyridyl |
| 167 | 4-F | 3-pyridyl |
| 168 | 4-F | 2-pyridyl |

TABLE 12-continued

[Structure: R₁-substituted phenyl attached to C(=O)-CH₂-piperidine-N-CH₂-Ar]

| Example | R1  | Ar          |
|---------|-----|-------------|
| 169     | 4-F | 2-pyrimidyl |
| 170     | 4-F | 4-pyrimidyl |
| 171     | 4-F | 2-quinolinyl|
| 172     | 4-F | 4-quinolinyl|
| 173     | 4-F | 2-naphthyl  |
| 174     | 4-F | 1-naphthyl  |

EXAMPLE 175

Methyl 3-(4'-Fluorophenyl)-4-oxo-4-(1''-benzylpiperidine)butyrate

A solution of 1-benzyl-4-(2'-(4''-fluorophenyl) acetyl)piperidine (0.54 g, 1.7 mmol) in anhydrous tetrahydrofuran (20 mL) was cooled to −78° C. with stirring under a nitrogen atmosphere. A solution of potassium bis(trimethylsilyl) amide in the toluene (0.5 M, 3.4 mL, 1.7 mmol) was added dropwise and the reaction mixture was stirred for 1.5 hours. Methyl bromoacetate (0.16 mL, 1.7 mmol) was added and the reaction mixture was warmed gradually to ambient temperature over 16 hours. The reaction mixture was poured onto brine, mixed, and extracted three times with ethyl acetate. The combined organic layers were dried over magnesium sulfate, filtered and concentrated in vacuo. Column chromatography (ethyl acetate) gave the product, a yellow oil (0.64 g): $^1$H-NMR:7.29-6.96(m,9H), 4.31(dd,1H,J=10,5), 3.62(s,3H), 3.45(s,2H), 3.18(dd,1H,J=17,10), 2.92-2.75(m,2H), 2.49(dd,1H,J=17,5), 2.45-2.39(m,1H), 1.96-0.88(m,6H); HR-MS:Calcd for $C_{22}H_{26}FNO_3$:383.1897; Found: 383,1907.

EXAMPLE 176

Methyl 3-(4'-Fluorophenyl)-4-oxo4-(1''-benzylpiperidino)butyrate, maleate salt

A saturated solution of maleic acid in ether (10 mL) was added to a solution of the product in Example 175 in ether (10 mL). The precipitate was filtered and washed with ether. Drying in vacuo gave a white powder:mp 119°-121° C.; Anal.:Calcd for $C_{23}H_{26}FNO_3 \cdot C_4H_4O_4$:C,64.92, H,6.05, N,2.80; Found: C,64.47, H,6.02, N,2.66.

EXAMPLE 177

3-(4'-Fluorophenyl)-2-(1''-benzyl4''-piperidino)propanenitrile

A solution of di-isopropylamine (0.56 g, 0.77 mL, 5.5 mmol) in anhydrous tetrahydrofuran (10 mL) was cooled to 0° C. with stirring under a nitrogen atmosphere. A solution of n-butyl lithium in hexanes (2.5 H,2.2 mL, 5.5 mmol) was added dropwise, then the reaction mixture was stirred for 15 minutes, then cooled to −78° C. A solution of 1-benzylpiperidine-4-acetonitrile (1.07 g, 1.05 mL, 5 mmol) in anhydrous tetrahydrofuran (5 mL) was added dropwise and then the reaction mixture was stirred for 1 hour. A solution of 4-fluorobenzylbromide (0.95 g, 0.62 mL, 5 mmol) in dry tetrahydrofuran (5 mL) was added dropwise. The reaction mixture was then warmed gradually to room temperature over 39 hours, poured onto water, mixed and extracted three times with ethyl acetate. The combined organic layers were dried over magnesium sulfate, filtered and concentrated in vacuo. Column chromatography (ethyl acetate) gave a yellow oil ($R_f$=0.41, 1.38 g): $^1$H-NMR:7.4-6.9(m,9H), 3.5 (s,2H), 3.05-2.55(m,5H), 2.05-1.5(m,7H); IR:3065(w), 3022(s), 2942(s), 2854(w), 2241(m), 1603(s), 1511(s), 1496(m), 1468(m), 1451(s), 1419(s); MS:322.

The product was converted to its hydrochloride salt by dissolving and bubbling hydrogen chloride gas through the solution. The precipitate was filtered and washed with ether. Drying in vacuo gave a white solid (1.19 g):mp >250° C.; $^1$H-NMR (DMSO-d6): 7.7-7.0(m,9H), 4.25(d,1H,J=2), 3.50-3.05(m,5H), 3.0-2.7(m,3H), 2.2-1.6(m,4H); Anal.:Calcd for $C_{21}H_{23}FN_2 \cdot HCl \cdot 0.2H_2O$: C,69.58, H,6.79, H,7.73; Found: C,69.51, H,6.66, N,7.57.

EXAMPLE 178

3-(4'-Fluorophenyl)-2-(1''-benzyl4''-piperidino) propaneamide

The product of Example 177 (1.0 g, 3.1 mmol) was mixed with a 6 N sodium hydroxide solution (20 mL) and ethanol (20 mL). The mixture was stirred at reflux temperature for 18 hours, then it was cooled to ambient temperature and acidified with a 2 N hydrochloric acid solution. The mixture was extracted three times with ethyl acetate and the combined organic layers were dried over magnesium sulfate, then filtered and concentrated in vacuo to yield a white powder (643 mg):mp 128°-130° C.; $^1$H-NMR: 7.4-7.3(m,5H), 7.2-7.1(m,2H), 7.0-6.9(m,2H), 5.35 (br s, 1H), 5.05(br s, 1H), 3.5(s,2H), 3.0-2.7(m, 4H), 2.2-1.25(m,9H); MS:340; Anal.:Calcd for $C_{21}H_{25}FN_2O \cdot 0.25H_2O$:C,73.12, H,7.45, N,8.12; Found: C,72.85, H,7.26, N,7.97.

EXAMPLES 179 TO 185

Examples 179 to 185 were or could be prepared by a combination of the procedures described above.

TABLE 13

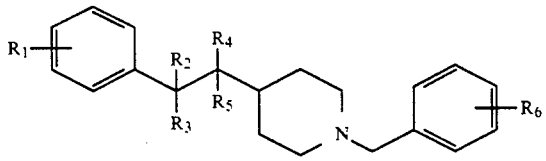

| Ex. | R1 | CR2R3 | CR4R5 | R6 | Salt | mp (°C.) |
|---|---|---|---|---|---|---|
| 175 | 4-F | C(H)(CH2CO2Me) | C(O) | H | | |
| 176 | 4-F | C(H)(CH2CO2Me) | C(O) | H | Maleate | 119–121 |
| 177 | 4-F | CH2 | C(H)(CN) | H | HCl | >250 |
| 178 | 4-F | CH2 | C(H)(CONH2) | H | | 128–130 |
| 179 | 4-F | CH2C(O) | CH2 | H | Maleate | 109–111 |
| 180 | 4-F | CH2 | C(H)(CO2H) | H | | |
| 181 | 4-F | C(CH3) | C—O | H | | |
| 182 | 4-F | CH2 | C(SC6H5) | H | | |
| 183 | 4-F | CH2 | CSO2C6H5 | H | | |
| 184 | 4-F | CH2 | C(SO2CH3) | H | | |
| 185 | 4-F | CH2 | C(CONMe2) | H | | |

EXAMPLE 186

1-(4'-Pyridylmethyl)-4-(2''-(4'''-Fluorophenyl)1''-oxoethyl)piperidine, maleate salt A mixture of 4-(2'-(4''-fluorophenyl)-1'-oxoethyl)-piperidine (0.4 g, 1.8 mmol), 4-picolyl chloride hydrochloride (0.33 g, 2 mmol), triethylamine (1.0 g, 1.4 mL, 10 mmol) and anhydrous tetrahydrofuran (10 mL) was stirred at reflux temperature for 20 h. The reaction mixture was cooled to room temperature, poured onto a 2N NaOH solution, mixed and extracted three times with ethyl acetate. The combined organic layers were dried over anhydrous magnesium sulfate and filtered. Solvent was removed in vacuo to give an oil (216 mg): $^1$H-NMR (CDCl$_3$, 200 MHz): 8.5(d,2H,J=6), 7.4-6.95(m,6H), 3.75(s,2H), 3.5(s,2H), 2.95-2.80(m,2H), 2.55-2.4(m,1H.2.15-1.6(m,8H); HRMS: Calcd for C$_{19}$H$_{21}$FN$_2$O:312.1638; Found:312.1642. (See Example 148).

The oil was dissolved in ether and the solution was treated with excess amount of a saturated solution of maleic acid in ether. An oily residue precipitated. Recrystallization from acetone-cyclohexane, filtration and drying in vacuo afforded the title compound, a tan solid (206 mg); mp 108°–109° C.; Calcd for C$_{19}$H$_{21}$FN$_2$O.2C$_4$H$_4$O$_4$.0.75H$_2$O: C,58.11, H,5.50, N,5.02; Found: C,57.82,57.76, H,5.34,5.24, N,4.49,4.53.

EXAMPLE 187

1-Phenethyl-4-(2'-(4''-fluorophenyl)-2'-oxoethyl)piperidine

A mixture of 4-(2'-(4''-fluorophenyl)-2'-oxoethyl)-pyridine (1.0 g, 4.65 mmol) and phenethylbromide (8.6 g, 6.3 mL, 46.5 mmol) was stirred at reflux temperature for 1.5 h. The reaction mixture was poured onto ether and mixed. The precipitate was filtered and washed with ether. The solid was dissolved in ethanol (100 mL). This solution was added to a suspension of Pt-black (prepared by hydrogenation of PtO$_2$ (0.1 g)) in ethanol (100 mL).

The mixture was shaken in a Parr apparatus under a hydrogen atmosphere (pressure ≦20 psi) until hydrogen uptake ceased (approximately 4 h). The mixture was filtered through Celite ® and solvent was removed in vacuo. The residue was treated with 1N NaOH and extracted three times with ethyl acetate. The organic layers were dried over MgSO$_4$ and concentrated. The residue was chromatographed twice (chloroform-methanol (9:1), then ethyl acetate) to give the title compound; a solid (120 mg): mp 73°–74° C.; $^1$H-NMR (CDCl$_3$, 300 MHz): 8.0(dd,2H,J=7,6), 7.3-7.1(m,7H), 3.0(br d.2H,J=9), 2.9(d,2H,J=7), 2.9-2.75(m,2H), 2.65-2.55(m,2H), 2.1-1.95(m,2H), 1.8(br d,2H,J=9), 1.6-1.2(m,3H); Anal.:Calcd for C$_{21}$H$_{24}$FNO·0.25H$_2$O: C,76.45, H,7.48, N,4.25; Found: C,76.56,76.83, H,7.51,7.44, N,4.26,4.28.

Examples 188 through 194 were or could be prepared according to the procedure described for Example 187 (Table 14).

TABLE 14

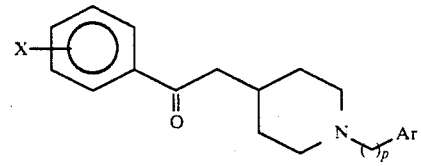

| Ex. No. | X | P | Ar | mp (°C.) |
|---|---|---|---|---|
| 187 | 4-F | 2 | C6H4 | 73–74 |
| 188 | 4-F | 2 | 4-FC6H4 | 96–98[a] |
| 189 | 4-F | 2 | 4-CF3C6H4 | 44–45[b] |
| 190 | 4-F | 1 | 2-naphthyl | 83–84[c] |
| 191 | 4-F | 2 | 4-CH3OC6H4 | 92–93[d] |
| 192 | 4-F | 2 | 4-ClC6H4 | 88–90[e] |
| 193 | 4-F | 1 | 4-FC6H4 | 67–68[f] |
| 194 | 4-F | 1 | 4-CF3C6H4 | 57–58[g] |

Notes for Table 14:
[a]Anal.:Calcd for C$_{21}$H$_{23}$F$_2$NO: C.73.45, H.6.75, N.4.08, F,11.06; Found: C,73.59, H,6.81, N,3.97, F,10.66.
[b]Anal.:Calcd for C$_{22}$H$_{23}$F$_4$NO: C,67.16, H.5.89, N,3.56, F,19.32; Found: C,67.07, H,6.13, N,3.44, F,19.03.
[c]Anal.:Calcd for C$_{24}$H$_{24}$FNO.0.25H$_2$O: C,78.60, H,6.73, N,3.82, F,5.18; Found: C,78.06,78.19, H,6.59,6.73, N,3.82,3.76, F,5.02.
[d]Anal.:Calcd for C$_{22}$H$_{26}$FNO$_2$.0.25H$_2$O: C.73.50, H.7.29, N,3.89, F,5.29; Found: C,73.59,73.63, H,7.26,7.22, N,3.65,3.64, F,4.89.
[e]Anal.:Calcd for C$_{21}$H$_{23}$ClFNO: C,70.89, H,6.44, N,3.89, F.5.28, Cl,9.85; Found: C,69.94, H,6.44, N,3.63, F,4.99, Cl,9.68.
[f]Anal.:Calcd for C$_{20}$H$_{21}$F$_2$NO: C,72.93, H,6.43, N,4.25, F,11.54; Found: C,72.90, H,6.17, N,3.80, F,11.34.
[g]Anal.:Calcd for C$_{21}$H$_{21}$F$_4$NO: C,66.48, H,5.58, N,3.69, F,20.03; Found: C,65.86, H,5.30, N,3.52, F,19.26.

EXAMPLE 195

1-Benzyl-4-(2'-(2''-naphthyl)-2'-hydroxyethyl)piperidine

According to the procedure described for Example 73C, 2-bromonaphthalene (3.8 g, 18.4 mmol), magnesium (0.45 g, 18.4 mmol) and 1-benzyl-4-formylmethylpiperidine (1.0 g, 4.6 mmol) were reacted to give the title compound, a solid (0.75 g), after chromatography (ethyl acetate, $R_f$=0.28): mp 33°–35° C.; Anal.:Calcd for $C_{24}H_{27}NO \cdot 0.5H_2O$: C,81.31, H,7.96, N,3.95; Found: C,81.66,81.82, H,7.78,7.84, N,3.45,3.46.

EXAMPLE 196

1-Benzyl-4-(2'-(2''-furyl)-2'-hydroxyethyl)piperidine

A solution of furan (0.68 g, 10 mmol) in anhydrous tetrahydrofuran (10 mL) was cooled to 0° C. with stirring under a nitrogen atmosphere. A solution of n-butyl lithium (2.1 M in hexanes, 4.8 mL, 10 mmol) was added dropwise via syringe. The reaction mixture was stirred for 30 min. at 0° C. A solution of 1-benzyl-4-formylmethylpiperidine (2.0 g, 9.2 mmol) in anhydrous tetrahydrofuran (5 mL) was added dropwise. The reaction mixture was warmed to ambient temperature overnight, poured onto a saturated ammonium chloride solution and extracted three times with ether. The combined organic layers were dried over anhydrous magnesium sulfate and filtered. Solvent was removed in vacuo. Column chromatography (chloroform:methanol: 9:1) of the residue gave the title compound, a solid (0.92 g): mp 118°–119° C.; $^1$H-NMR (CDCl$_3$, 300 MHz): 7.4-7.2(m,6H), 6.3(d,2H,J=8), 4.8(m,1H), 3.5(s,2H), 2.8(br d,2H,J=7), 2.0-1.2(m,10H); Anal.:Calcd for $C_{18}H_{23}NO_2 \cdot 0.25H_2O$: C,74.58, H,8.17, N,4.83; Found: C,74.91,74.92, H,8.17,8.13, N,4.61,4.58.

EXAMPLE 197

1-Benzyl-4-(2'-(2''-thienyl)-2'-hydroxyethyl)piperidine

According to the procedure described for Example 196, thiophene (0.84 g, 10 mmol), n-butyl lithium (2.1 M in hexanes, 4.8 mL, 10 mmol) and 1-benzyl-4-formylmethyl piperidine (2.0 g, 9.2 mmol) were reacted to give the title compound, a solid (2.05 g) after chromatography (chloroform-methanol (9:1)): mp 118°–120° C.; Anal.:Calcd for $C_{18}H_{23}NOS \cdot 0.25H_2O$: C,70.66, H,7.74, N,4.58, S,10.48; Found: C,71.12,71.09, H,7.65,7.73, N,4.65,4.65, S,10.02,9.99.

EXAMPLE 198

1-Benzyl-4-(2'-(4''-hydroxyphenyl)-2'-oxoethyl)piperidine

A mixture of 1-benzyl-4-(2'-(4''-t-butyldimethylsilyloxyphenyl)-2'-oxoethyl)piperidine (Example 75, 1.21 g, 2.86 mmol), a solution of tetra-n-butylammonium fluoride (1.0 M in tetrahydrofuran, 5.7 mL, 5.7 mmol) and tetrahydrofuran (10 mL) were stirred at ambient temperature under a nitrogen atmosphere overnight. The reaction mixture was poured onto water and extracted three times with ethyl acetate. The combined organic layers were dried over anhydrous magnesium sulfate, filtered and concentrated in vacuo. The residue was triturated with ethyl acetate and filtered. Drying in vacuo gave the title compound (238 mg): mp 197°–198° C.; $^1$H-NMR (CDCl$_3$, 300 MHz): 7.8(d,2H,J=8), 7.4-6.8(m,7H), 3.5(s,2H), 3.2-3.0(br s,4H), 3.0-2.8(dd,4H,J=10,7), 2.5(s,1H), 2.1-1.2(m,4H); Anal.:Calcd for $C_{20}H_{23}NO_2 \cdot 0.25H_2O$: C,76.53, H,7.55, N,4.40; Found: C,76.63,76.54, H,7.47,7.31, N,4.23,4.26.

EXAMPLE 199

1-Benzyl-4-(2'-(4'''-hydroxymethylphenyl)-2'-oxoethyl)-piperidine

Following the procedure described for Example 198, 1-benzyl-4-(2'-(4'''-t-butyldimethylsilyloxyphenylmethyl)-2'-oxoethyl)piperidine (Example 118, 177 mg, 0.4 mmol) was converted to the title compound, which was purified by trituration with ether and dried in vacuo (45 mg): mp 154°–155° C.; Anal.:Calcd for $C_{21}H_{25}NO_2 \cdot 0.5H_2O$: C,75.87, H,7.88, N,4.21; Found: C,75.94,75.79, H,7.74,7.80, N,3.85,4.09.

EXAMPLES 200 AND 201

1-Benzyl-4-(2'-(4''-methylsulfonylphenyl)-2'-oxoethyl)-piperidine (Example 200) and 1-Benzyl-4-(2'(4''-methylsulfinylphenyl)-2'-oxoethyl)-piperidine (Example 201)

A mixture of 1-benzyl-4-(2'-(4''-methylthiophenyl)-2'-oxoethyl)piperidine (Example 50, 2.18 g, 6.4 mmol), sodium periodate (13.7 g, 64.2 mmol), 32.5 mL methanol and 32.5 mL water was stirred at room temperature overnight. The mixture was diluted tenfold with water, basified with a 1.0 N NaOH solution and extracted three times with ether. The combined organic layers were dried over anhydrous magnesium sulfate and filtered. Solvent was removed in vacuo. Column chromatography (chloroform-methanol (9:1)) gave the title sulfone (Example 200, 165 mg, $R_f$=0.63): mp 135°–137° C.; MS: 371; Anal.:Calcd for $C_{21}H_{25}NO_3S$: C,67.90, H,6.78, N,3.77, S,8.63; Found: C,67.88, H,6.74, N,3.69, S,8.63.

Further elution gave the title sulfoxide (Example 201, 690 mg, $R_f$=0.5): mp 135°–136° C.; MS: 355; Anal.:Calcd for $C_{21}H_{25}NO_2S \cdot 0.25H_2O$: C,70.06, H,7.14, N,3.89, S,8.91; Found: C,70.14,70.32, H,6.89,6.94, N,3.70,3.66, S,8.89.

EXAMPLE 202

1-Benzyl-4-(2'-(2''-naphthyl)-2'-oxoethyl)piperidine

Following the procedure described for Example 109, 1-benzyl-4-(2'-(2''-naphthyl)-2'-hydroxyethyl)piperidine (0.5 g, 1.45 mmol) was converted to the title compound (230 mg): mp 118°–119° C.; Anal.:Calcd for $C_{24}H_{25}NO$: C,83.93, H,7.34, N,4.08; Found: C,83.67, H,7.19, N,4.02.

EXAMPLE 203

1-Benzyl-4-(2'-(6''-fluoroquinol-2''-yl)-1-hydroxyethyl)-piperidine, hydrochloride salt A solution of di-isopropylamine (0.55 g, 5.5 mmol) in anhydrous tetrahydrofuran (5 mL) was cooled to 0° C. with stirring. A solution of n-butyl lithium (2.5 M in hexanes, 2 mL, 5 mmol) was added dropwise. The solution was stirred at 0° C. for 15 min. A solution of 6-fluoroquinaldine (0.81 g, 5 mmol) in anhydrous tetrahydrofuran (5 mL) was added dropwise. The reaction mixture was stirred at 0° C. for 30 min., then a solution of 1-benzyl-4-formylpiperidine (1.0 g, 4.9 mmol) in anhydrous tetrahydrofuran (5 mL) was added. Tetramethylethylenediamine (0.58 g, 5 mmol) was added. The reaction mixture was warmed gradually to room temperature over 24 h, poured onto water and extracted three times with ethyl acetate. The combined organic layers were dried over magnesium sulfate and filtered. Solvent was removed in vacuo to give a liquid. Column chromatography (chloroform:methanol::9:1) gave 1- benzyl-4-(2'-(6''-fluoroquinolin-2-yl)-2'-1-hydroxyethyl)-piperidine (591 mg): $^1$H-NMR (CDCl3, 200 MHz): 8.1-7.9(m,2H), 7.55-7.25(m,8H), 5.65-5.4(m,1H), 4.05-3.95(m,1H), 3.5(s,2H), 3.25-2.9(m,4H), 2.1-1.45(m, 7H); HRMS:Calcd for $C_{23}H_{25}FN_2O$:361.1951, Found:364.1953.

The product was dissolved in ether (10 mL) and treated with a solution of HCl in ether (1.0 M, 10 mL). The precipitate was filtered and washed with ether. Drying in vacuo afforded the title compound, a solid (377 mg): mp 205°-207° C.; Anal.:Calcd for $C_{23}H_{25}FN_2O \cdot 2HCl \cdot 2H_2O$: C,58.53, H,6.60, N,5.92, Cl,14.97; Found: C,58.53,58.38, H,6.23,6.24, N,6.23,6.24, N,5.74,5.84, Cl,15.11,15.21.

EXAMPLE 204

1-Benzyl-4-(2'-(4''-pyridyl)-1'-hydroxyethyl)piperidine

Following the procedure described for Example 203, 4-picoline (0.93 g, 10 mmol) was converted to the title compound, an oil: $^1$H-NMR (CDCl3, 200 MHz): 8.5(d,2H, J=6), 7.4-7.1(m,7H), 4.6-4.5(m,1H), 3.5-3.45(m,1H), 3.5 (s,2H), 3.1-2.8(m,3H), 2.6(dd,1H,J=8,6), 2.0-1.25 (m, 7H); HRMS:Calcd for $C_{19}H_{24}N_2O$:296.1888; Found:296.1891.

TABLE 15

Ar—CR²R³—CR⁴R⁵—piperidine—N—Ar'

| Ex. No. | Ar | Ar' | CR²R³ | CR⁴R⁵ | mp (°C.) |
|---|---|---|---|---|---|
| 195 | 2-naphthyl | $C_6H_5$ | C(H)(OH) | $CH_2$ | 33-35 |
| 196 | 2-furyl | $C_6H_5$ | C(H)(OH) | $CH_2$ | 118-119 |
| 197 | 2-thienyl | $C_6H_5$ | C(H)(OH) | $CH_2$ | 118-120 |
| 198 | 4-hydroxyphenyl | $C_6H_5$ | C(O) | $CH_2$ | 197-198 |
| 199 | 4-hydroxymethylphenyl | $C_6H_5$ | C(O) | $CH_2$ | 154-155 |
| 200 | 4-methylsulfonylphenyl | $C_6H_5$ | C(O) | $CH_2$ | 135-137 |
| 201 | 4-methylsulfinylphenyl | $C_6H_5$ | C(O) | $CH_2$ | 135-136 |
| 202 | 2-naphthyl | $C_6H_5$ | C(O) | $CH_2$ | 118-119 |
| 203 | 6'-fluoroquinol-2-yl | $C_6H_5$ | $CH_2$ | C(H)(OH) | |
| 204 | 4-pyridyl | $C_6H_5$ | $CH_2$ | C(H)(OH) | |

EXAMPLE 205

1-(4'-Pyridylmethyl)-4-(2''-4'''-fluorophenyl)1''-oxoethyl)piperidine, dimaleate salt Following the procedure for Example 134, the product of Example 148 was treated with maleic acid in ether to give the title compound: mp 108°-109° C.; Anal.:Calcd. for $C_{19}H_{21}FN_2O \cdot 2C_4H_4O_4 \cdot 0.75$ $H_2O$: C,58.11, H,5.50, N,5.02; Found: C,57.82,57.76, H,5.34,5.24, N,4.49,4.53.

UTILITIES SECTION

The compounds of this invention and their pharmaceutically acceptable salts possess psychotropic properties, particularly antipsychotic activity of good duration with selective sigma receptor antagonist activities while lacking the typical movement disorder side-effects of standard dopamine receptor antagonist antipsychotic agents. These compounds may also be useful as antidotes for certain psychotomimetic agents such as phencyclidine (PCP), and as antidyskinetic agents.

IN VITRO

Sigma Receptor Binding Assay

Male Hartley guinea pigs (250-300 g. Charles River) were sacrificed by decapitation. Brain membranes were prepared by the method of Tam (Proc. Natl. Acad. Sci. USA 80: 6703-6707, 1983). Whole brains were homogenized (20 seconds) in 10 vol (wt/vol) of ice-cold 0.34 M sucrose with a Brinkmann Polytron (setting 8). The homogenate was centrifuged at 920×g for 10 minutes. The supernatant was centrifuged at 47,000×g for 20 minutes. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000×g for 20 minutes and resuspended in 50 mM Tris HCl (50 mL per brain).

0.5 mL aliquots of the membrane preparation were H incubated with unlabeled drugs, 1 nM (+)-[$^3$H]SKF 10,047 in 50 mM Tris HCl, pH 7.4, in a final volume of 1 mL. Nonspecific binding was measured in the presence of 10 μM (+)-SKF 10,047. The apparent dissociation constant (Kd) for (+)-[$^3$H]SKF 10,047 is 50 nM. After 45 minutes of incubation at room temperature, samples were filtered rapidly through Whatman GF/C glass filters under negative pressure, and washed 3 times with ice-cold Tris buffer (5 mL).

IC$_{50}$s were calculated from log-logit plots. Apparent Ki's were calculated from the equation, Ki=IC$_{50}$/[1+(L/K$_d$)](4), where L is the concentration of radioligand and K$_d$ is its dissociation constant. Data are shown in Table I.

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [$^3$H]spiperone in a final volume of 1 mL containing 50 mM Tris HCl, 120 mM NaCl and 1 mM MgCl2 (pH 7.7). Nonspecific binding was measured in the presence of 100 nM (+)-butaclamol. After 15 minutes of incubation at 37° C., samples were filtered rapidly through Whatman GF/C glass filters under negative pressure, and washed three times with ice-cold binding buffer (5 mL).

IC$_{50}$s were calculated from log-logit plots. Apparent Ki's were calculated from the equation Ki=IC$_{50}$[1+(L/K$_d$)](4), where L is the concentration of radioligand and Kd is its dissociation constant. Data are shown in Table I.

The data in Table I indicate that haloperidol, a typical antipsychotic drug, has potent binding affinity for both the sigma and dopamine receptors. This binding profile of haloperidol reflects the therapeutic activity as well as the motor side effects caused by antagonism of the dopamine receptors. In contrast, the examples of this invention shown in Table I indicate potent and selective binding affinity for sigma receptors without binding to the dopamine receptors or only have weak binding for the dopamine receptors. Therefore these compounds are not expected to produce the extrapyramidal symptoms that are typical of that produced by haloperidol and other typical antipsychotics that are dopamine receptor antagonists.

IN VIVO

Isolation-Induced Aggression in Mice

This is a modification of the method of Yen et al. (Arch. Int. Pharmacodyn. 123: 179-185, 1959) and Jannsen et al. (J. Pharmacol. Exp. Ther. 129: 471-475, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 minutes. Isolated mice failing to consistently attack an intruder were eliminated from the colony.

Drug testing was carried out by treating the isolated mice with test drugs or standards. Fifteen minutes after dosing with test drugs by the oral route, one isolated mouse was removed from its home cage and placed in the home cage of another isolate. Scoring was a yes or no response for each pair. A maximum of 3 minutes was allowed for an attack and the pair was separated immediately upon an attack. Selection of home cage and intruder mice was randomized for each test. Mice were treated and tested twice a week with at least a 2 day washout period between treatments.

As shown in Table II, haloperidol and Examples 104, 34 and 205 all have potent activities in inhibiting the isolation-induced aggressive behavior indicating psychotropic activities.

(+)-N-Allylnormetazocine-Induced Turning Behavior in Rats

Male Sprague-Dawley rats (CDICR, Charles River), weighing 190-290 g, were used for surgery. In order to spare nonadrenergic neurons, rats were injected with 25 mg/kg imipramine i.p. 30 minutes before surgery. The rats were anesthetized with a 1:1.2 ratio mixture of Xylazine:Ketamine given 0.1 mL/100 g body weight i.m. A Ringers-Wydaze (100:0.01) solution was given to prevent dehydration. Dopamine was depleted in the right striatum by injecting the neurotoxin 6-hydroxydopamine (6-OHDA) into the substantia nigra of the right cerebral hemisphere. Five mg of 6-OHDA was dissolved in 5 mL of a 0.04% ascorbic acid solution which had been deoxygenated with nitrogen. Five µL of the 6-OHDA solution was injected into the substantia nigra through a 26 gauge needle over a five minute period. Stereotaxic injection coordinates were −2.5 mm posterior to bregma, −2.1 mm right of the midsagittal suture, and −8.6 mm below the skull surface with the incisor bar set at +5.0 mm. Following surgery they were given 10 days to recover while housed four per cage (45.0 L×20.0 H×26.0 W) with ALPHA-dri bedding and ad lib access to Pro-Lab rodent chow and deionized water. Following recovery, the wood clips were removed, the rats were individually housed in suspended cages, and they were placed on a restricted diet so that their weight did not exceed 375 g. At all times they were housed in the animal care facility under a 12-12 hour light/dark cycle (light on at 6:00 h, light off at 18:00 h).

Rotation rate and direction were determined with Coulbourn Instruments Rotometry Monitors. Clockwise and counter clockwise rotations were recorded at 30 and 60 minute intervals. The rats were examined for correct lesion location by testing for rotational activity induced by s.c. injections of 3.0 mg/kg D-amphetamine SO$_4$, and 4.0 mg/kg (+)-N-allylnormetazocine, respectively. These drugs were administered in the following sequence: Amphetamine was given 30 second before testing. Seven days later, the rats were injected with (+)-N-allylnormetazocine 30 seconds before testing. Only those rats with an ipsilateral rotation rate of 2.5 turns per minute or higher were used in subsequent tests.

Methocel or test drugs were administered either orally (p.o.) or subcutaneously (s.c.) 20 minutes before testing. (+)-N-allylnormetazocine (4.0 mg/kg) was given s.c. immediately before testing.

The data were analyzed with an analysis of variance statistical test and individual comparisons of each dose of test drug to control were made with Dunnett's multiple range test. The ED$_{50}$ was calculated with a Litchfield and Wilcoxon test using percent of control values. As shown in Table III both haloperidol and Example 134 potently antagonized the sigma hallucinogen N-allylnormetazocine-induced rotation in this rat model. The hallucinogen PCP also has significant affinity for the sigma receptor (Tam, *Eur. Pharmacol,* 109:33-41 (1985)).

TABLE I

| | In Vitro Receptor Binding Affinities | |
|---|---|---|
| Example | Sigma | Dopamine (D-2) |
| Haloperidol | +++ | +++ |
| 177 | +++ | + |
| 104 | +++ | − |
| 68 | +++ | − |
| 38 | +++ | − |
| 134 | +++ | − |
| 179 | +++ | − |
| 205 | +++ | − |
| 203 | ++ | − |
| 5 | − | |
| 10 | +++ | − |
| 80 | +++ | − |
| 106 | +++ | − |
| 108 | +++ | − |
| 133 | +++ | − |
| 113 | +++ | − |
| 116 | +++ | − |
| 198 | +++ | − |
| 89 | ++ | − |
| 76 | +++ | − |
| 195 | +++ | − |
| 112 | +++ | − |
| 117 | +++ | − |
| 202 | +++ | + |
| 199 | ++ | − |
| 42 | +++ | − |
| 72 | +++ | − |
| 187 | +++ | ++ |
| 188 | +++ | ++ |
| 189 | +++ | N.T. |
| 190 | +++ | + |
| 191 | +++ | N.T. |
| 192 | +++ | N.T. |
| 193 | +++ | − |
| 194 | +++ | + |
| 196 | +++ | N.T. |
| 197 | +++ | N.T. |

N.T. = Not Tested

TABLE II

| | In Vivo |
|---|---|
| Example | Inhibition of Isolation-induced Aggression |
| Haloperidol | +++ |
| 104 | + |

TABLE II-continued

| | In Vivo |
|---|---|
| Example | Inhibition of Isolation-induced Aggression |
| 134 | +++ |
| 205 | + |

TABLE III

| | In Vivo |
|---|---|
| Example | Inhibition of (+)-N-Allylnor-metazocine Induced Turning |
| Haloperidol | +++ |
| 134 | +++ |

DOSAGE FORMS

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in Remington's Pharmaceutical Sciences, A. Osol, 17th Edition (1985) a standard reference text in this field.

What is claimed is:

1. A method of treating physiologic or drug induced psychosis or dyskinesia in a mammal comprising administering to the mammal an antipsychotic or antidyskinetic affective amount of a compound of the formula:

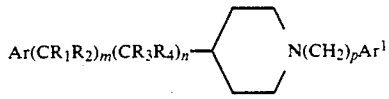

or a pharmaceutically acceptable salt thereof wherein:
$R_1$ and $R_3$ independently are H, alkyl of 1–3 carbon atoms, OH, or alkoxy of 1–3 carbon atoms;
$R_2$ and $R_4$ independently are H, or alkyl of 1–3 carbon atoms;
$CR_1R_2$ or $CR_3R_4$ may be C=O, provided that both cannot be C=O;
Ar and $Ar^1$ independently are phenyl optionally substituted with 1–5 substituents independently selected from the group consisting of:
H, halogen, OH, alkoxy of 1–3 carbon atoms, $NR_{10}R_{11}$, SH, $S(O)_t$, $R_{12}$ where t=0–2, haloalkyl of 1–3 carbon atoms and 1–7 halogen atoms, alkyl of 1–3 carbon atoms, $CO_2H$, carboalkoxy of 2–6 carbon atoms, $CO_2NR_{13}R_{14}$, CN, $NO_2$, $SO_2NH_2$, OR $SO_3H$;
or Ar and $Ar^1$ independently are naphthyl optionally substituted with H, halogen, or alkyl of 1 to 3 carbon atoms;
$R_{10}$ to $R_{14}$ independently are H or alkyl of 1 to 3 carbon atoms;
m and n independently are 1–5; and
p is 1–2.

2. A method of claim 1 wherein m plus n is 2 or

3. A method of claim 1 wherein the compound is 1-Benzyl-4-(2'-(4"-fluorophenyl)-2'-hydroxyethyl) piperidine, or the hydrochloride salt thereof.

4. A method of claim 1 wherein the compound is 1-Benzyl-4-(2'-(4"-fluorophenyl)-2'-oxoethyl) piperidine, or the maleate s thereof.

5. A method of claim 1 wherein the compound is 1-Benzyl-4(2'-(4"-fluorophenyl)-1'-oxoethyl)piperidine, or the maleate salt thereof.

6. A method of claim 1 wherein the compound is 1-(4'-Pyridylmethyl)-4-(2'-4 "-fluorophenyl)-1-oxoethyl)piperidine, or the maleate salt thereof.

* * * * *